United States Patent
Stickler et al.

(10) Patent No.: US 8,211,832 B2
(45) Date of Patent: Jul. 3, 2012

(54) HERBICIDAL GLYPHOSATE COMPOSITION

(75) Inventors: Chris A. Stickler, Windsor, CO (US); Randall Worthley, Greeley, CO (US)

(73) Assignee: Loveland Products, Inc., Greeley, CO (US)

( * ) Notice: Subject to any disclaimer, the term of this patent is extended or adjusted under 35 U.S.C. 154(b) by 236 days.

(21) Appl. No.: 12/747,133

(22) PCT Filed: Dec. 9, 2008

(86) PCT No.: PCT/US2008/086052
§ 371 (c)(1), (2), (4) Date: Jun. 9, 2010

(87) PCT Pub. No.: WO2009/076349
PCT Pub. Date: Jun. 18, 2009

(65) Prior Publication Data
US 2010/0261607 A1    Oct. 14, 2010

Related U.S. Application Data

(60) Provisional application No. 61/012,543, filed on Dec. 10, 2007.

(51) Int. Cl.
*A01N 57/20* (2006.01)
*A01P 13/00* (2006.01)
(52) U.S. Cl. ..................................................... 504/206
(58) Field of Classification Search ............... None
See application file for complete search history.

(56) References Cited

U.S. PATENT DOCUMENTS
5,668,085 A    9/1997    Forbes et al.
2002/0160916 A1    10/2002    Volgas et al.

FOREIGN PATENT DOCUMENTS
EP    0068295    1/1983
WO    WO 98/35561    8/1998
WO    WO 2005/011380    2/2005

OTHER PUBLICATIONS

Leaper, C. et al., "Adjuvants and Glyphosate Activity", Pest Management Service, vol. 56, No. 4, Apr. 1, 2000, 313-319.
Barnes, Jeff W. et al., "Cloransulam adsorption, translocation, and efficacy on common broadleaf weed species", Weed Science, 52:634-641 (2004).
International Search Report and Written Opinion issued in PCT/US2008/086052, mailed Jul. 9, 2010, 15 pages.
Chilean Resolution No. 2987, Department of Agriculture, with English Translation, 2007.

*Primary Examiner* — Johann R. Richter
*Assistant Examiner* — Daniel L Branson
(74) *Attorney, Agent, or Firm* — Faegre Baker Daniels LLP

(57) ABSTRACT

The present invention relates to exogenous compositions and methods of their use, wherein the exogenous chemicals are applied to one or more surface layers of plants to generate a herbicidal biological response and in particular to a glyphosate-based herbicidal composition for spray application to a plant having superior properties of herbicidal cuticle layer coating and penetration, herbicidal uptake, and herbicidal translocation, without cuticle layer damage.

5 Claims, 1 Drawing Sheet

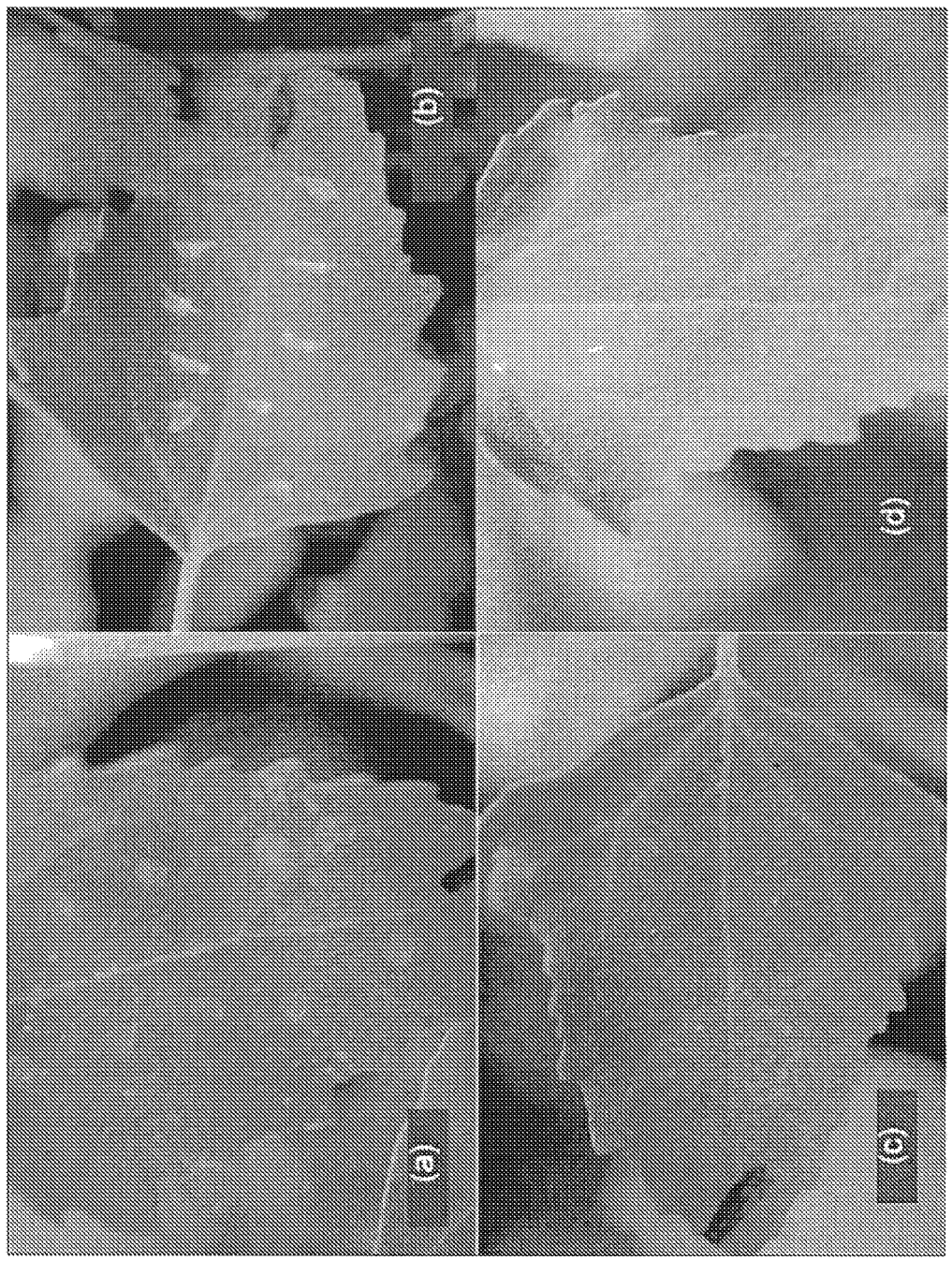

HERBICIDAL GLYPHOSATE COMPOSITION

CROSS-REFERENCE TO RELATED APPLICATIONS

The present application is a national phase application of PCT/US2008/086052, filed pursuant to 35 U.S.C. §371, which claims priority to U.S. 61/012,543, filed Dec. 10, 2007. Both applications are incorporated herein by reference in their entirety.

FIELD OF THE INVENTION

The invention relates generally to a glyphosate composition and in particular to a herbicidal glyphosate composition for treating a plant, having superior herbicidal properties of cuticle layer penetration, uptake, translocation, and efficacy, without cuticle layer damage.

BACKGROUND OF THE INVENTION

This invention relates to compositions and methods for enhancing the spraying efficacy of exogenous chemicals used in spray-treating plants. An exogenous chemical, as defined herein, is any chemical substance, whether naturally or synthetically derived, which (a) has biological activity or is capable of releasing in a plant an ion, moiety, or derivative which has biological activity, and (b) is applied to a plant with the intent or result that the chemical substance or its biologically active ion, moiety, or derivative enter living cells or tissues of the plant and elicit a stimulatory, inhibitory, regulatory, therapeutic, toxic, or lethal response in the plant itself or in a pathogen, parasite, or feeding organism present in or on the plant. Examples of exogenous chemical substances include, but are not limited to, chemical pesticides (such as herbicides, fungicides, or insecticides), plant growth regulators, fertilizers and nutrients or mixtures thereof.

Various combinations of exogenous chemicals (e.g., foliar-applied herbicides) and surfactants or other adjuvants have been, and are currently, used, so that when water is added, the resulting sprayable composition is more easily and effectively retained on the foliage (e.g., the leaves or stems) of plants. Through this, and perhaps other effects, surfactants have been known to increase the biological effectiveness of herbicide compositions, or other compositions of exogenous chemicals, when added to, or included in, such compositions of exogenous chemicals. For example, the herbicide glyphosate (N-phosphonomethylglycine) has been formulated with surfactants such as polyoxyalkylene-type surfactants including, among other surfactants, polyoxyalkylene alkylamines. Surfactants have generally been combined with glyphosate or other exogenous chemicals either in a commercial concentrate or in a diluted mixture (e.g., a tank mix) that is prepared from separate compositions, one comprising an exogenous chemical (e.g., glyphosate) and another comprising surfactant, prior to use in the field.

Many exogenous chemicals are commercially packaged as a liquid concentrate that contains a significant amount of water. The concentrate is diluted by adding water in accordance with instructions. The prepared, dilute composition is then sprayed onto plants.

Some surfactants tend to degrade fairly rapidly in aqueous solutions. As a result, surfactants that exhibit this property can only be used effectively in tank mixes (i.e., mixed with the other ingredients in solution or dispersion in the tank soon before spraying is to occur), rather than being formulated in an aqueous composition with the other ingredients in the first instance. This lack of stability, or inadequate shelf-life, has hindered the use of certain surfactants in some exogenous chemical formulations.

Other surfactants, though chemically stable, are physically incompatible with certain exogenous chemicals, particularly in concentrate formulations. For example, most classes of nonionic surfactants, including polyoxyethylene alkylether surfactants, do not tolerate solutions of high ionic strength, as for example in a concentrated aqueous solution of a salt of glyphosate. Physical incompatibility can also lead to inadequate shelf-life. Other problems that can arise from such incompatibility include the formation of aggregates large enough to interfere with commercial handling and application, for example by blocking spray nozzles.

Two important application properties of a sprayable composition having exogenous chemicals and surfactants are its spray-dispersion particle-size distribution and the spray dispersion's adherence to the plants being sprayed. Small droplet-size dispersions tend to drift from the intended target plants so that larger droplet-size dispersions are preferred. While larger droplet-size dispersions drift less and deliver more composition to the plant, if the larger droplets adhere poorly to the foliage surface, the large droplets can aggregate on the foliage, causing a high variability in coating the foliage, or even run off the plant, wasting some of the composition and reducing cost-effectiveness of the spray method.

One consequence of the above-described variability in coating is that foliar-applied exogenous chemicals are typically applied at significantly higher rates than needed to give the desired biological effect in the particular situation where they are used, to allow for the natural variability that exists in efficiency of foliar uptake. A need therefore exists for sprayable compositions of exogenous chemicals that substantially remain on the contacted plant foliage and are efficiently uptaken and translocated, thereby allowing reduced use rates.

A need also exists for improved formulations of exogenous chemicals, particularly herbicides, that are stable and effective, coat foliage well, and for stable liquid concentrate formulations of exogenous chemicals that contain less water and more exogenous chemical than prior art concentrates.

Genetically modified crop plants (e.g., corn, soybeans) can be resistant to uptaken herbicides such as glyphosate so that an area having these plants plus undesirable weeds (e.g., lambsquarter, velvetleaf, giant ragweed) should be able to be spray treated with a glyphosate formulation so that only the weeds are eradicated. However, many formulations of glyphosate sprays inflict damage to the cuticle layer of the genetically modified crop plants, resulting in stress and reduced yield. There is, therefore, also a need for a herbicidal formulation that does not, or at least minimizes, damage to the cuticle layer of sprayed, desirable crop plants.

SUMMARY OF THE INVENTION

The present invention relates to exogenous compositions and methods of their use, wherein the exogenous chemicals are applied to one or more surface layers of plants to generate a herbicidal biological response and in particular to a glyphosate-based herbicidal composition for spray application to a plant having superior properties of herbicidal cuticle layer coating and penetration, herbicidal uptake, and herbicidal translocation, without cuticle layer damage.

One embodiment of the present invention is a plant treatment composition comprising (a) an exogenous chemical comprising N-phosphonomethylglycine or its herbicidal derivatives, (b) a first adjuvant that is an amphiphilic surfactant, and (c) a second adjuvant that enhances adherence of the composition to plant foliage. The weight/weight ratio of said first and second adjuvants combined to the exogenous chemical is between about 1:10 and about 4:10, and in the presence of water, the composition contacts a surface or layer (e.g., a plant leaf) and resists running off the layer. This composition can be used in a method of treating plants, in which foliage of the plant is contacted with a biologically effective amount of a composition as described herein and further comprising an aqueous-based diluent.

DESCRIPTION OF THE DRAWING

FIG. 1 is an electronic image of plants treated with herbicidal compositions.

DETAILED DESCRIPTION

An especially preferred group of exogenous chemicals used in the invention is N-phosphonomethylglycine and its herbicidal derivatives. N-phosphonomethylglycine, referred to herein by its common name glyphosate, can be used in its acid form, or in forms that are water-soluble, such as a salt. The term "water-soluble" in this context means having a solubility in distilled water at 25° C. greater than about 1% by weight. Suitable water-soluble exogenous chemical salts have an anion portion and a cation portion. More commonly it is the anion portion that is biologically active.

Any water-soluble salt of glyphosate may be used in the practice of this invention. Suitable salts include the isopropylamine; sodium; potassium; ammonium; mono-, di-, tri- and tetra-$C_{1-4}$-alkylammonium; mono-, di- and tri-$C_{1-4}$-alkanolammonium; mono-, di- and tri-$C_{1-4}$-alkylsulfonium; and sulfoxonium salts. Particularly suitable salts are the isopropylamine, ammonium, monoisopropyl-ammonium, and trimethylsulfonium salts of glyphosate. Mixtures of salts can also be useful in certain situations. A commercial formulation of the isopropylamine salt of glyphosate is available from Monsanto Co., St. Louis, Mo. and Dow Agrosciences, LLC, Indianapolis, Ind., which comprises about 62% by weight of the active glyphosate isopropylamine salt.

In an embodiment, the composition can be a shelf-stable concentrate composition comprising the exogenous chemical substance in an amount of about 10% to about 90% by weight. The term "shelf-stable" in this context means that the composition does not exhibit phase separation when stored at ambient temperature for a period of time dependent on the particular circumstances. Such shelf-stable concentrates of the invention can be embodied as, for example, a composition that further comprises a liquid diluent, wherein the composition comprises the exogenous chemical substance in an amount of about 10% to about 60% by weight. In this embodiment, the exogenous chemical substance is water-soluble and present in an aqueous-based phase of the composition in an amount of about 30% to about 50% by weight of the composition. This composition can be, for example, an aqueous-based solution concentrate.

A composition of the present invention comprising an exogenous chemical, a first adjuvant, and a second adjuvant, as described above, can have a number of different physical forms, for example, a water-soluble concentrate. The composition may further comprise water in an amount effective to make the composition a dilute, aqueous-based composition ready for application to foliage of a plant. The inventive composition may contain from about 1% by weight of the exogenous chemical up to about 45% by weight, or even more, of the exogenous chemical.

In one embodiment, the invention is an aqueous-based spray composition having the properties that it substantially adheres well to an exposed surface or layer of plant foliage; insubstantially runs off of the layer; substantially penetrates the surface or layer (e.g., cuticle layer) with no or very little damage to the surface or layer; is uptaken well, and translocates well. This embodiment of the composition comprises an exogenous chemical, an aqueous-based diluent, a first adjuvant which is amphiphilic, and a second adjuvant which enhances adherence of the composition to a wax layer. In a sprayable composition of this embodiment, the weight/weight ratio of the first and second adjuvants combined to the exogenous chemical is between about 1:10 and about 4:10. The term "spray composition" is sometimes used herein to mean a sprayable composition.

In another embodiment of the invention, the first adjuvant is a liposome-forming material that comprises an amphiphilic compound or mixture of such compounds having two hydrophobic moieties, each of which is a saturated alkyl or acyl chain having from about 8 to about 22 carbon atoms. The amphiphilic compound or mixture of such compounds having two hydrophobic moieties with about 8 to about 22 carbon atoms constitutes from about 40% to 100% by weight of all amphiphilic compounds having two hydrophobic moieties present in the liposome-forming material. Preferably the liposome-forming material has a hydrophilic head group comprising a cationic group. In some embodiments, the cationic group is an amine or ammonium group. Examples of such liposome-forming materials include fatty acids (e.g., arachidic acid, arachidonic acid, lauric acid, linolenic acid, myristic acid, oleic acid, palmitic acid, palmitoleic acid, or stearic acid), fatty-acid esters (e.g., methyl laurate, methyl linolenate, methyl oleate, methyl palmitate, or methyl palmitoliate), phospholipids, or phospholipid derivatives (e.g., phosphatides, lyso-phosphatides). Suitable phosphatides are generally a phosphoric ester that on hydrolysis yields phosphoric acid, fatty acid(s), polyhydric alcohol(s), and, typically, a nitrogenous base. A phosphatide component may be present in a partially hydrolyzed form, e.g., as phosphatidic acid. Suitable phosphatides include phosphatidylcholine, lyso-phosphatidylcholine, hydrogenated phosphatidylcholine, phosphatidylinositol, phosphatidylserine, phosphatidic acid, phosphatidylglycerol, phosphatidylethanolamine, N-acyl phosphatidylethanolamine or mixtures of any of these. These liposome-forming materials may be found in plant and animal sources but are commonly and economically found in vegetable oils, such as soybean oil and sunflower oil, and are commercially available in substantially pure or mixture forms. Some suitable non-ionic surfactants (e.g., ethylene oxylates) may also be used.

In this other embodiment of the invention, the second adjuvant comprises a foliage-adherence-enhancing material, such as an amine ethoxylate blend, available from Huntsman Petrochemical Corp., The Woodlands, Tex.

In various embodiments of the invention, a concentrate composition is provided which, upon dilution, dispersion, or dissolution in aqueous-based diluents, forms a sprayable composition. The concentrate composition contains a reduced amount of the aqueous-based diluent, or, in a particular embodiment, is a dry composition having less than about 5% water by weight. Typically, a concentrate composition of the invention contains at least about 10% by weight of the exogenous chemical, or more specifically from about 35% to about 45% by weight.

One particular combination of first and second adjuvants, hereafter referred to as Adjuvant Combination, that is set out in Table 1 provides a glyphosate composition with the desirable properties of shelf stability in concentrate or ready-to-use composition, sprayability, foliar retention, cuticle layer penetration without damage to the cuticle layer, herbicidal efficacy, and cost-effectiveness. Table 1 describes the materials in one embodiment of an Adjuvant Combination given as the materials' approximate ("ca.") weight percent relative to the total weight of Adjuvant Combination materials.

TABLE 1

| Material | ca. Weight % |
|---|---|
| dinonylphenylpolyoxyethylene | 0.0725 |
| non-fatty acids: | 1.1788 |
| rosin acids (e.g., abietic-type acids, pimaric-type acids) | |
| phosphatidic acid | |
| fatty acid esters: | 1.5629 |
| methyl arachidiate | |
| methyl laurate | |
| methyl linoleate | |
| methyl linolenate | |
| methyl myristate | |
| methyl oleate | |
| methyl palmitate | |
| methyl palmitoliate | |
| methyl stearate | |
| fatty acids: | 5.7579 |
| arachidic acid | |
| lauric acid | |
| linoleic acid | |
| linolenic acid | |
| myristic acid | |
| oleic acid | |
| palmitic acid | |
| palmitoleic acid | |
| stearic acid | |
| phosphatidylethanolamine | 2.5914 |
| lyso-phosphatidylethanolamine | 0.0362 |
| phosphatidylcholine | 5.9992 |
| lyso-phosphatidylcholine | 0.1637 |
| phosphatidylinositol | 3.0543 |
| phosphatidylserine | 0.0725 |
| ethylene glycol | 5.3882 |
| polyethylene glycol | 0.1762 |
| poly-(oxy-1,2-ethanediyl)-alpha-undecyl-omega | 1.5306 |
| poly(oxy-1,2-ethanediyl), alpha-(4-nonylphenyl)-omega-hydroxy-, branched | 7.0175 |
| water | 10.266 |
| hydroacrylic acid | 15.3057 |
| alkyl amine ethoxylate(s) | 39.8261 |
| | 100.0000 |

Nonlimiting examples of embodiments of the invention are set forth in the EXAMPLES section below.

EXAMPLES

Example 1

| Material | ca. Weight % |
|---|---|
| glyphosate isopropylamine salt (commercial formulation) | 66.13 |
| water | 18.37 |
| TERWET ® 3780* | 7.50 |
| Adjuvant Combination | 8.00 |
| | 100.00 |

Example 2

| Material | ca. Weight % |
|---|---|
| glyphosate isopropylamine salt (commercial formulation) | 66.13 |
| water | 17.87 |
| TERWET ® 3780* | 8.00 |
| Adjuvant Combination | 8.00 |
| | 100.00 |

Example 3

| Material | ca. Weight % |
|---|---|
| glyphosate isopropylamine salt (commercial formulation) | 66.13 |
| water | 17.87 |
| TERWET ® 3780* | 7.50 |
| Adjuvant Combination | 8.00 |
| nonylphenylethyleneoxylate* | 0.50 |
| | 100.00 |

Example 4

| Material | ca. Weight % |
|---|---|
| glyphosate isopropylamine salt (commercial formulation) | 66.0 |
| water | 18.0 |
| Adjuvant Combination | 16.0 |
| | 100.0 |

Example 5

| Material | ca. Weight % |
|---|---|
| glyphosate isopropylamine salt (pure) | 41.0 |
| water | 43.0 |
| Adjuvant Combination | 16.0 |
| | 100.0 |

*This material can be obtained from Huntsman Petrochemical Corp., The Woodlands, TX.

The glyphosate isopropylamine salt commercial formulation in the foregoing EXAMPLES includes about 62% by weight active glyphosate isopropylamine salt. In Example 5, the glyphosate isopropylamine salt commercial formulation is presumed to be 62% by weight glyphosate isopropylamine salt and 38% by weight water. The amount of a formulation having a glyphosate isopropylamine salt weight percent different from 62% by weight glyphosate isopropylamine salt can be adjusted by stoichiometric proportioning so that about the appropriate amount of active glyphosate isopropylamine salt is achieved.

For treatment of acreage of plants to be eradicated, aerial spraying is an economical method of applying the inventive composition. Given the herbicidal effect of the inventive composition, ideally the spray of the inventive composition reaches only the targeted plants. For crop plants genetically modified to be resistant to an uptake of glyphosate herbicide, a crop area having both such a genetically modified crop plant and weeds to be eradicated, the whole area may be sprayed with an embodiment of the inventive composition to eradicate the weeds without causing cuticle layer damage to the crop plants.

For aerial spraying, aerial drift from the targeted plants must be minimized to avoid harming desirable plants sensitive to a glyphosate herbicide. One factor to reduce aerial drift is the spray droplet size, where larger droplets drift less than smaller droplets. Several factors affect the droplet size. Orienting spray nozzles so that the spray is released parallel to the air stream produces larger droplets than other orientations. Nozzles providing higher flow rates produce larger droplets than lower flow rate nozzles. Nozzles having a narrower spray angle produce larger droplets. For many nozzle types, while higher pressure increases the flow rate, lower pressure produces larger droplets. Therefore, where higher flow rates are desired, it is preferable to use lower pressure with a higher flow rate nozzle than to use increased pressure with a lower flow rate nozzle. The droplet size, generally described by droplet diameter, will not be identical for all droplets, but rather controllable to a range of droplet diameters suitable for particular plants and spraying conditions.

Another embodiment of the present invention is a method of spray applying the inventive composition to a plant, comprising the steps of (a) providing a pressure-based spraying apparatus comprising a container that holds the composition to be sprayed and an orientable spray nozzle in fluid communication with the composition in the container that provides a flow rate and a spray angle of the composition to be sprayed and a dispersion of suitable, sprayed-droplet sizes; (b) placing an amount of the composition into the container; (c) providing pressure to the composition to be sprayed; and (d) producing and orienting the direction of a sprayed dispersion of suitable droplet sizes of the composition so that the sprayed dispersion contacts foliage of a targeted plant. The method further comprises using a pressure, flow rate, spray angle, and orientation that produce a spray of droplet sizes that resists aerial drifting. The method further comprises using a pressure, flow rate, spray angle, and orientation that produces a spray of suitable droplet sizes of the herbicidal composition of the present invention.

EFFICACY TESTS

Uptake efficacy testing of embodiments of the inventive composition was done by using $C^{14}$ isotope substitution in the glyphosate molecule and monitoring the uptake of the $C^{14}$-isotope-substituted glyphosate molecule by analysis for systemic presence of the $C^{14}$-doped glyphosate molecule. For cuticle damage and uptake efficacy testing, a leaf or leaves to be treated with an embodiment of the inventive composition is first covered with metal foil (e.g., aluminum foil) and then the plant(s) was oversprayed with the embodiment of the inventive composition. Then, controlled droplets (usually 10-20 droplets) of the embodiment of the inventive composition having $C^{14}$-isotope-substituted glyphosate were applied to the top surface of the plant leaf or leaves. The quantity of droplets of $C^{14}$-isotope-substituted glyphosate inventive composition was that which produced at least about 200,000 disintegrations per minute ("dpm") from the $C^{14}$-doped glyphosate molecules. The treated leaf or leaves was washed off at predetermined intervals, harvested, dried, and combusted in an oxidizer. The combustion gas containing $C^{14}$-isotope is captured, and the dpm of the combustion gas is counted by a scintillation counter of suitable sensitivity to the $C^{14}$-isotope. A method of $C^{14}$-doping analysis is generally described in Jeff W. Barnes, Lawrence R. Oliver, "Cloransulam absorption, translocation, and efficacy on common broadleaf weed species", *Weed Science*, 52:634-641 (2004), incorporated herein by reference. Herbicidal efficacy testing of the inventive composition was also done by several U.S. universities.

The difference in cuticle damage between the inventive composition and current commercial compositions is shown in FIG. 1. FIGS. 1(*a*), (*b*) show cuticle damage where about ten droplets of two commercial glyphosate compositions were applied. FIG. 1(*c*) shows no cuticle damage where about ten droplets of an embodiment of the inventive composition was applied. FIG. 1(*d*) shows no cuticle damage where an aqueous solution of glyphosate was applied.

The preceding description of specific embodiments of the present invention is not intended to be a complete list of every possible embodiment of the invention or to otherwise limit the scope of the invention. Persons of ordinary skill in the art of this field will realize that modifications can be made to the specific embodiments described herein that would be within the scope of the present invention.

The invention claimed is:

1. A composition for treating a plant comprising
   (a) an exogenous chemical;
   (b) a first adjuvant;
   (b) a second adjuvant; and
   (c) an aqueous-based diluent,
   wherein the exogenous chemical is from about 35% to about 45% by weight glyphosate isopropylamine salt; the first adjuvant comprises at least two fatty acids, at least two fatty-acid esters, hydroacrylic acid, a phospholipid, a phospholipid derivative, a glycol, and a polyoxyethylene; and the second adjuvant comprises an amine ethoxylate, further wherein the at least two fatty acids and at least two fatty-acid esters have a saturated alkyl or acyl chain from about 8 carbon atoms to about 22 carbon atoms.

2. The composition of claim 1 comprising from about 35% to about 45% by weight of the aqueous-based diluent; and from about 10% to about 20% by weight of the first and second adjuvants combined.

3. The composition of claim 1 which provides substantial uptake, translocation, and efficacy of the exogenous chemical, and insubstantial damage to a cuticle layer of the plant treated with the composition.

4. A method of spraying a composition comprising
   (a) an exogenous chemical;
   (b) a first adjuvant;
   (b) a second adjuvant; and
   (c) an aqueous-based diluent,
   wherein the exogenous chemical is from about 35% to about 45% by weight glyphosate isopropylamine salt the first adjuvant comprises at least two fatty acids, at least two fatty-acid esters, hydroacrylic acid, a phospholipid, a phospholipid derivative, a glycol, and a polyoxyethylene; and the second adjuvant comprises an amine ethoxylate, further wherein the at least two fatty acids and at least two fatty-acid esters have a saturated alkyl or acyl chain from about 8 carbon atoms to about 22 carbon atoms, the method of spraying comprising the steps of
   (a) providing a pressure-based spraying apparatus comprising a container that holds the composition to be sprayed and an orientable spray nozzle in fluid communication with the composition in the container that provides a flow rate and a spray angle of the composition to be sprayed and a dispersion of suitable, sprayed-droplet sizes;
(b) placing an amount of the composition into the container;
(c) providing pressure to the composition to be sprayed; and
(d) producing a sprayed dispersion of suitable droplet sizes of the composition.

5. The method of claim 4 wherein the produced spray dispersion contacts foliage of a targeted plant.

\* \* \* \* \*